United States Patent [19]
Johnson

[11] Patent Number: 4,488,814
[45] Date of Patent: Dec. 18, 1984

[54] APPARATUS FOR AND METHOD OF OPTICAL ABSORBANCE AND FLUORESCENT RADIATION MEASUREMENT

[75] Inventor: Leighton C. Johnson, Edwardsburg, Mich.

[73] Assignee: Miles Laboratories, Inc., Elkhart, Ind.

[21] Appl. No.: 306,206

[22] Filed: Sep. 28, 1981

[51] Int. Cl.³ .................. G01J 3/50; G01N 21/64; G01N 21/03
[52] U.S. Cl. .................. 356/414; 250/576; 356/417; 356/440; 356/236; 356/246
[58] Field of Search .............. 356/244, 246, 432, 436, 356/440, 409, 414, 417, 236; 73/864.13, 864.14; 250/576; 34/95; 422/100; 436/49

[56] References Cited
U.S. PATENT DOCUMENTS

| | | | |
|---|---|---|---|
| 2,026,267 | 12/1935 | Brandlin | 356/246 |
| 2,027,518 | 1/1936 | Cornell et al. | 356/246 X |
| 2,042,255 | 5/1936 | Haas | 34/95 UX |
| 2,090,427 | 8/1937 | Sample | 34/95 |
| 3,246,559 | 4/1966 | Clifford, Jr. | 356/246 |
| 3,699,348 | 10/1972 | Höcherl | 250/576 |
| 3,838,926 | 10/1974 | Kato et al. | 356/236 X |

FOREIGN PATENT DOCUMENTS 55-26454 2/1980 Japan .................. 356/246

OTHER PUBLICATIONS

Levine et al., *IBM Technical Disclosure Bulletin*, vol. 18, No. 11, Apr. 1976, pp. 3754-3756.

*Primary Examiner*—F. L. Evans
*Attorney, Agent, or Firm*—Joseph C. Schwalbach; Roger Norman Coe

[57] ABSTRACT

Apparatus and method for biological fluid analysis involving radiation measurement. The apparatus includes a pipetting dispenser having means for directing radiation from the piston thereof generally axially through the liquid in the pipette tube such that the pipetting dispenser serves not only as a means for measuring and mixing liquids, but also serves as a cuvette. The apparatus and method provide maximum radiation path length to accommodate liquids of different optical density. Still another feature of the apparatus and method is the provision of means for removing liquid from the outer surface of a pipette tube, which means are readily adapted to automated procedures. The apparatus in one embodiment is adapted for absorbance measurement of analyte samples, and in another embodiment is adapted for measurement of fluorescent radiation from analyte samples.

36 Claims, 10 Drawing Figures

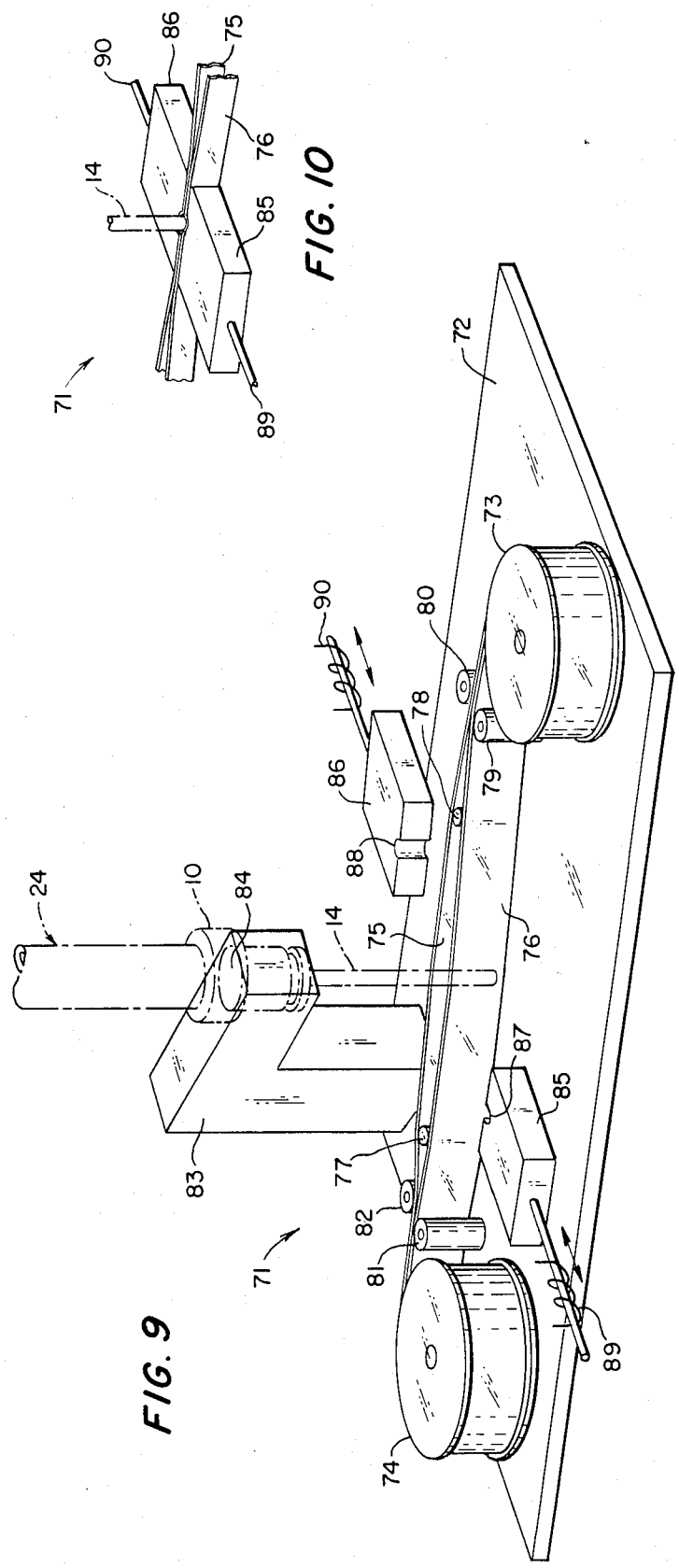

APPARATUS FOR AND METHOD OF OPTICAL ABSORBANCE AND FLUORESCENT RADIATION MEASUREMENT

BACKGROUND OF THE INVENTION

This invention relates in general to the field of clinical chemistry, and more particularly to the analysis of biological fluids for the presence or absence of certain biochemical components.

One common method for such analysis involves mixing a precisely measured small volume of liquid analyte sample with a precisely measured small volume of one or more liquid reagents, incubating the mixture, measuring the optical absorbance of the incubated mixture, and comparing it with the optical absorbance of the sample measured prior to mixing with reagent.

Another method of analysis involves, instead of optical absorbance measurement, the measurement of fluorescent radiation resulting from flash-type monochromatic irradiation of a fluorescent analyte sample. Absorption of radiant energy by the molecules of the analyte raises the vibrational level of such molecules from the ground state to one of the excited electronic levels. The absorption step occurs within $10^{-15}$ seconds, and the fluorescence results from the spontaneous radiative transition that occurs when the molecules of the analyte return to the ground electronic state upon termination of the incident radiation. The resulting fluorescent light is given off equally in all directions at a wavelength different from that of the exciting light, and with an intensity which is orders of magnitude lower than that of the incident light.

In carrying out analyses by the foregoing methods, the known art utilizes various combinations of precision liquid pipetting devices, pumps, mixers, light sources, light detectors, cuvettes and pipette cleaning means. Sample and reagent volumes are typically measured in precision pipetting devices and are mixed in a mixing receptacle. After incubation of the mixed sample and reagent, as necessary, the pipetting device is used to transfer the incubated mixture to a cuvette for absorbance measurement.

Typical of the general type of precision pipetting device known in the art are those disclosed in Drummond, et. al., U.S. Pat. No. 3,606,086, and Allen, U.S. Pat. No. 3,815,790. Devices of this type include an elongated cylindrical barrel, at one end of which a pipette tube is coaxially mounted. A plunger or piston is axially movable within the pipette tube and is carried by a spring-loaded holder movable axially within and projecting from the other end of the barrel.

Typical cuvettes used in the art accommodate a substantial volume of the liquid analyte whose absorbance is to be photometrically measured. The length of the optical path through such cuvettes is fixed (e.g., 1 cm.), and because only a limited beam passes through the cuvette, only a limited portion of the analyte in the cuvette is actually exposed to the incident beam. Moreover, during such measurement, a substantial amount of the irradiating light is lost through the sides of conventional cuvettes due to scattering. Because the optical path through conventional cuvettes is fixed, if a liquid analyte is too dense to be measured in a given cuvette, either the liquid must be diluted, or a cuvette with a shorter optical path must be used.

Because precision measurement of liquids by pipetting devices requires that liquid adhering to the outer surface thereof be removed, various means have been developed for wiping such surfaces, as by causing the pipette to pierce, or to pass through a hole of smaller diameter formed in, a layer of bibulous material. The procedures thus far developed have not, however, been of a type which is well adapted to automation.

SUMMARY OF THE INVENTION

With the foregoing in mind, it is a principal object of the present invention to provide an improved apparatus and method for radiation measurement involving the use of precision liquid pipetting device which also functions as a cuvette.

Another object of the invention is to provide an improved apparatus and method of the class described wherein nearly all of the analyte in the pipette/cuvette is subjected to the incident light.

A further object of the invention is to provide an improved apparatus and method of the aforementioned character in which the longest possible optical path length for a given volume of analyte is provided, and the irradiation of the liquid is maximized by multiple internal reflections through the liquid, which reflections also minimize light loss.

Another object of the invention is to provide an improved apparatus and method as aforedescribed wherein the volume of the analyte and the optical path length therethrough can be precisely and infinitely varied to accommodate the optical density of the particular analyte, so that neither dilution of the analyte, nor substitution of cuvettes need be resorted to.

A still further object of the invention is to provide an improved apparatus and method of the class described wherein novel means adaptable to automated procedures are used to remove liquid from the outer surface of the pipette tube to insure precision volumetric and radiation measurement.

Another object of the invention is to provide an improved apparatus and method of the character described wherein the optical path through the liquid in the pipette tube extends in a direction generally axially of the tube from a piston therein toward the outer end of the tube.

A more specific object of the invention is to provide an improved apparatus and method as aforedescribed wherein the pipette piston incorporates light source means and comprises one end portion of a light guide, which guide extends externally of the pipette/cuvette and is adapted to receive radiation from from a source thereof.

Another specific object of the invention is to provide an improved pipette/cuvette which is well adapted for use in either optical absorbance or fluorescent radiation measurements of liquid analyte samples.

As the description proceeds with reference to the accompanying drawings, other and further objects and advantages of the invention will become apparent to those skilled in the art.

BRIEF DESCRIPTION OF THE DRAWINGS

FIG. 9 is a perspective semi-diagrammatic view of another form of the portion of the apparatus by which liquid is removed from the outer surface of a pipette tube, part of the pipette/cuvette being shown in phantom lines.

FIG. 10 shows a fragment of FIG. 9 and illustrates the pressing of the absorbent tapes around the lower end of the pipette tube by the movable pressure members.

DESCRIPTION OF THE PREFERRED EMBODIMENT

Figure 1:
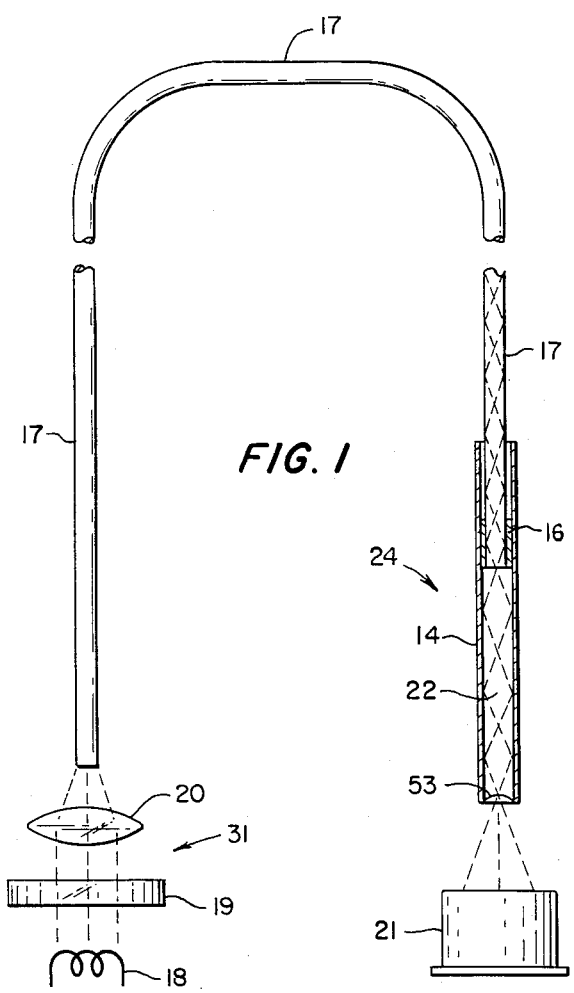
FIG. 1 is a semi-diagrammatic showing of parts of the apparatus of the present invention illustrating the optics of the embodiment thereof adapted for optical absorbance measurement.

In describing the invention, reference will be had first in FIG. 1, which illustrates diagrammatically the optics of the embodiment thereof adapted for optical absorbance measurement. More particularly, a liquid analyte sample 22, the absorbance of which is to be measured, is contained in a cylindrical tube 14, for example, of glass, quartz or clear plastic, in which a piston 16 is movable. Incorporated with piston 16 is one end of a fiber optic light guide 17, the other end of which is positioned to receive radiation from a light source 18. Interposed between light source 18 and the fiber optic guide member 17 are a filter 19 and a condensing lens 20. The lower end of the tube 14 is aligned with and directed toward a radiation detector 21, which may take the form of photodiode, which is connected to suitable readout means (not shown), which may include a picoammeter (also not shown).

Figure 2:
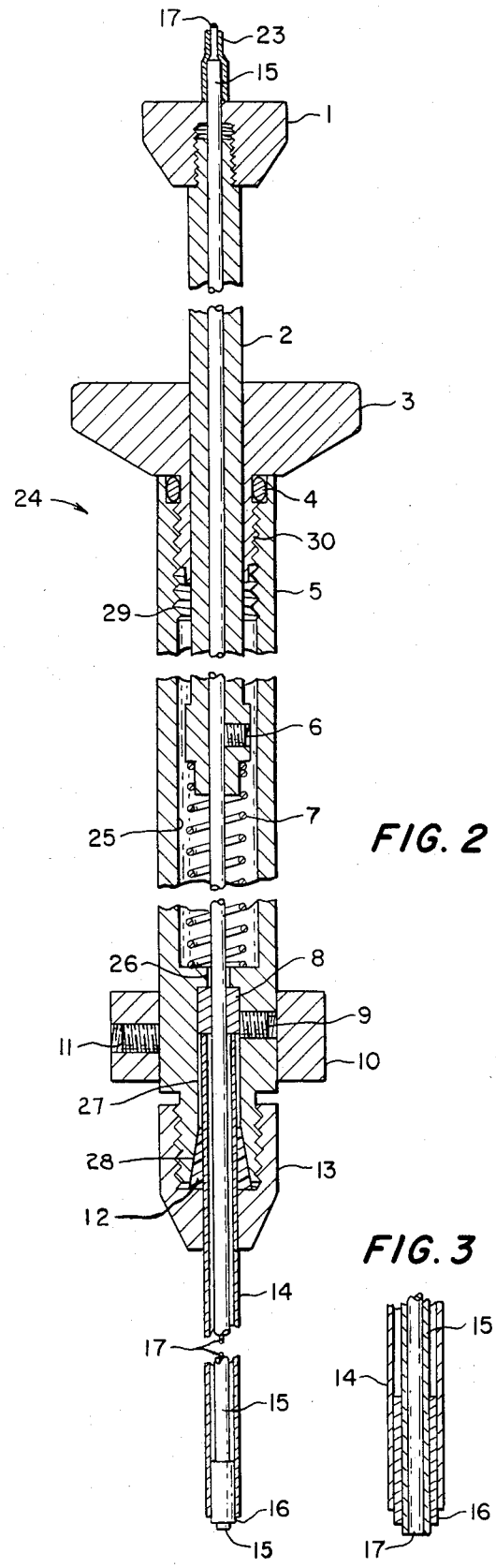
FIG. 2 is a vertical sectional view of the pipette/cuvette portion of the apparatus of the present invention.

For a more specific description of the apparatus of the present invention, reference is made to FIG. 2, wherein a portion of the improved apparatus which shall be characterized as a pipette/cuvette 24 is shown in axial section. Those skilled in the art will recognize that the pipette/cuvette 24 resembles a Drummond-type precision liquid pipetting device of the general type shown in U.S. Pat. No. 3,815,790.

Device 24 comprises a tubular barrel 5 having in its upper end portion an axial bore 25 which terminates at its lower end in a reduced diameter bore 26. Bore 26, in turn, communicates with a bore 27 which terminates at its lower end an outwardly flared frusto-conical bore portion 28. The upper end of the barrel 5 is internally threaded, as at 29, to receive the externally threaded portion of the tubular stem 30 of a barrel cap 3. An O-ring 4 may be provided to seal the juncture between the cap 3 and barrel 5.

Axially slidable within the barrel cap 3 and axially movable within the barrel 5 is a tubular plunger 2 having a cap 1 threaded on the upper end thereof as shown. The plunger 2 is biased upwardly by a helical spring 7 which, at its upper end, engages concentric shoulder means on the plunger 2, and at its lower end is seated in the lower end of the bore 25 as shown.

Seated within the bore 27 adjacent the bore 26 is a guide bushing 8 which is held in place by a set screw 9. A glass tube 14 extends coaxially within the bore 27 and engages the annular outer end surface of bushing 8. The lower end of the barrel 5 is externally threaded to receive an internally threaded compression nut 13 through which the tube 14 extends, and a tapered resilient tubular compression fitting 12 surrounds the tube 14 within the tapered bore 28. The compression nut 13 and compression fitting 12 cooperate to hold the tube 14 coaxially within the bore 27 as shown.

Figure 3:
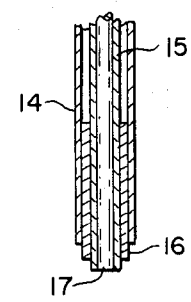
FIG. 3 is an enlarged vertical sectional view of the lower end of the device shown in FIG. 2.

Extending coaxially through the plunger cap 1, plunger 2, barrel 5, and glass tube 14 is a light guide means which in the preferred form of the invention is a fiber optic member. A plastic core, plastic-clad single fiber optic rod purchased from Poly Optics, Inc., Santa Ana, Calif., and having a diameter of 0.025 inch has been found to function satisfactorily in the embodiment of the present invention adapted for optical absorbance measurement. Within the device 24 the fiber optic light guide member 17 is preferably encased in a tubular stainless steel sheath 15. At its lower end, the encased light guide member 17 is incorporated within a piston 16 slidable within the tube 14. The piston may take the form of a cylindrical Teflon ® sleeve press fitted onto the lower end of the stainless steel tubular sheath 15 as shown in FIG. 3. The light guide member 17 and its metal sheath 15 are fixed within the plunger 2 by means of a set screw 6 as shown. In FIG. 2 the piston 16 is shown in its lowermost position, it being understood that unless the plunger 2 is restrained, the spring 7 will actuate the plunger 2 upwardly to thereby retract the piston 16 within the glass tube 14.

The tubular sheath 15 surrounding the light guide member 17 has a coaxial sliding fit within the bushing 8, and at its upper end terminates a short distance above the plunger cap 1 as shown. The light guide member 17 extends to the light source means assembly 31 shown in detail in FIG. 4. The portion of the guide member 17 extending between the device 24 and the assembly 31 is encased within a flexible tubular sheath 23 which may be made of opaque polyvinyl chloride or other suitable material. The light guide member 17 is preferably sufficiently flexible to permit free movement of the device 24 in the use thereof. However, it will be understood that the metal sheath 15 imparts rigidity to the portion of the light guide member 17 within the device 24 and functions as a piston rod for the piston 16.

Figure 4:
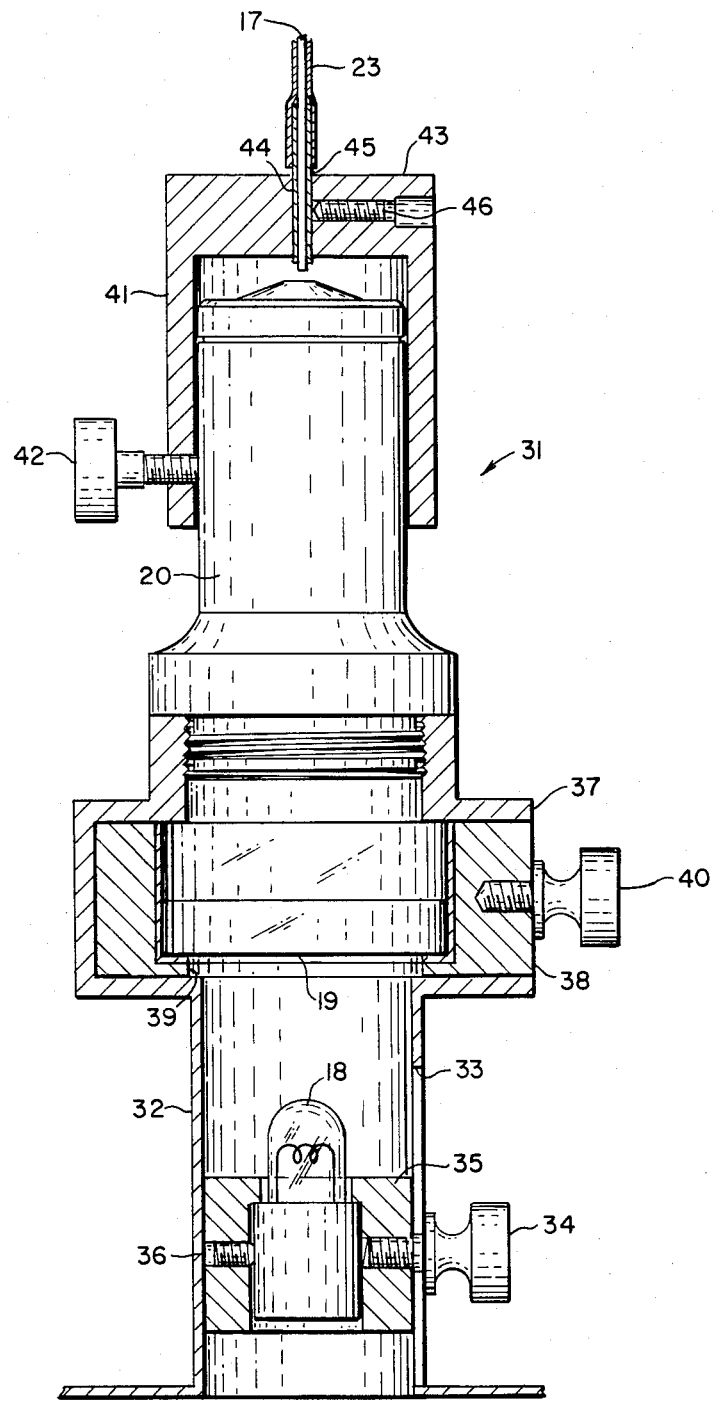
FIG. 4 is a view, partly in vertical section, of the light source means portion of the apparatus of the present invention.

Referring now to FIG. 4, the light source assembly 31 illustrated therein comprises a tubular base member 32 formed with an axially extending slot 33 to accommodate a thumb screw 34 which is threaded into a cylindrical light source support sleeve 35. The sleeve 35 has a light source 18 fixed therein, as by a set screw 36. In the embodiment of the invention adapted for absorbance measurement, the source 18 may take the form of an incandescent lamp, and more particularly lamp No. 3027 available from the General Electric Company. It is apparent that by releasing the thumb screw 34, the position of sleeve 35, together with source 18, may be vertically adjusted. It can then be resecured in the adjusted position by tightening the thumb screw 34.

The base member 32 is formed at its upper end with a rectangular enlargement 37 to accommodate a drawer-like filter holder 38, having an aperture 39 in its bottom wall. The filter holder 38 is provided with a knob 40 to permit withdrawal thereof and placement therein of a light filter 19 as shown. The presently preferred form of filter 19 for use in absorbance measurements is a two-cavity interference type filter having a wavelength of 500 nanometers and one-half band width of 12 nanometers.

The upper end of the base member 32 is internally threaded to receive the external thread on the lower end portion of a condenser lens assembly 20 mounted coaxially thereon. The illustrated lens assembly 20 may take the form of a microscope objective lens such as Unitron No. 43732, coated, 100x, oil immersion, and having a numerical aperture of 1.25. Coaxially mounted on the upper end of the lens assembly 20 is an inverted cup-shaped member 41. A thumb screw 42 extends through the wall of the member 41 as shown, and engages the lens assembly 20 to secure the member 41 thereto. Adjustment of the axial position of the member 41 with respect to the assembly 20 can be accomplished upon loosening the thumb screw 42, and retightening the thumb screw will secure said member in the new position to which it is moved.

The cup-shaped member 41 has a transverse wall 43 which is formed with an axial bore 44 to receive the end portion of the light guide member 17 associated therewith. An extent of metallic sheath 45, similar to the metallic sheath 15 in FIG. 2, encases the portion of the light guide member 17 extending through the bore 44, said sheath extending upwardly from the wall 43 a short distance as shown. The light guide member 17 and its sheath 45 are secured within the wall portion 43 by a set screw 46 as shown.

It will be observed that the end portion of the light guide member 17 within the cup-shaped member 41 is coaxially aligned with the condenser lens assembly 20 and terminates a short distance from the upper end thereof. The axial distance between the end portion of light guide member 17 and the lens assembly 20 is adjustable by adjustment of the axial position of the cup member 41 with respect to assembly 20 as aforementioned, said distance being chosen to insure maximum concentration of light from the source 18 onto the adjacent end of the light guide member 17.

Figure 5:
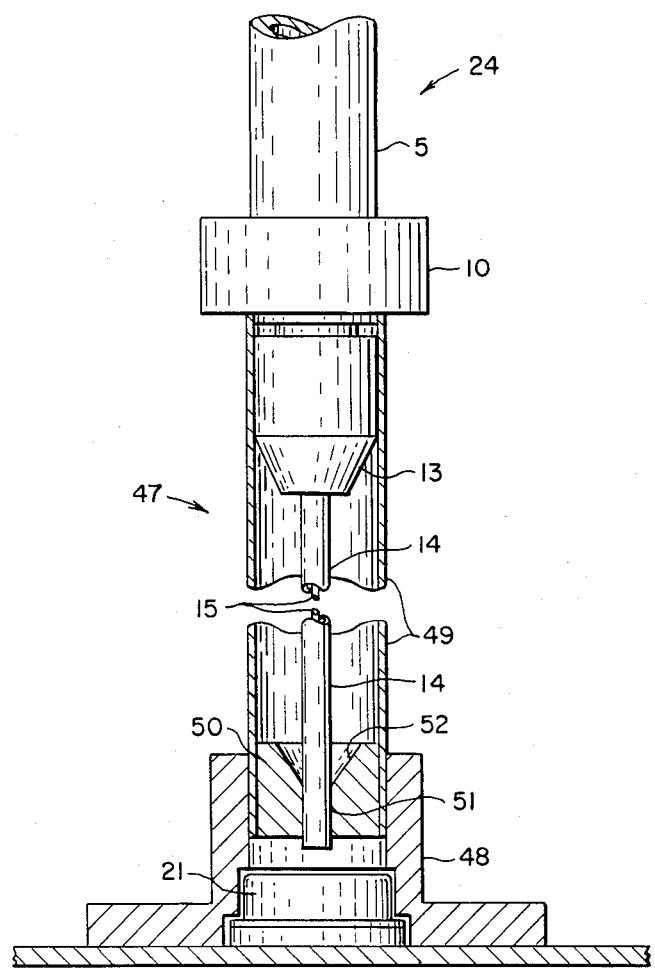
FIG. 5 is a vertical sectional view taken through the radiation measurement fixture portion of an embodiment of the present invention adapted for optical absorbance measurement, part of the pipette/cuvette being shown in operative position within said fixture.

Referring now to FIG. 5, there is illustrated therein a fixture 47 which forms a part of an embodiment of the invention adapted for absorbance measurements. The fixture 47 comprises a tubular base member 48 having a barrel member 49 telescopically fitted into the upper end therof. The base 48 is formed with a suitable cavity for accommodation of a radiation sensing device 21 which, for absorbance measurements, may be a photodetector of the type identified as EG & O UV-360B 9/21. Fixed within the lower end of the barrel 49 is a cylindrical guide member 50 having a bore 51 of a size to slidably receive the glass tube 14 of device 24, the bore 51 communicating at its upper end in an outwardly flared frusto-conical bore 52. As shown in FIG. 5, the pipette/cuvette device 24 can be coaxially placed on the upper end of the barrel 49, and if the lower end of the tube 14 of device 24 engages the surface of the tapered bore 52 during such placement, it is guided thereby into the bore 51.

The position of the lower end of the tube 14 with respect to the photodetector 21 is determined by the position of a collar 10 which engages the upper end of barrel 49 and is adjustably fixed coaxially on the barrel 5 of device 24 by a set screw 11 shown in FIG. 2. The set screw 11 permits adjustment of the position of the collar 10 on the barrel 5 of device 24, and thereby the spacing between the end of the tube 14 and photodetector 21, when the device 24 is supported on the fixture 47 as shown in FIG. 5.

Figure 8:
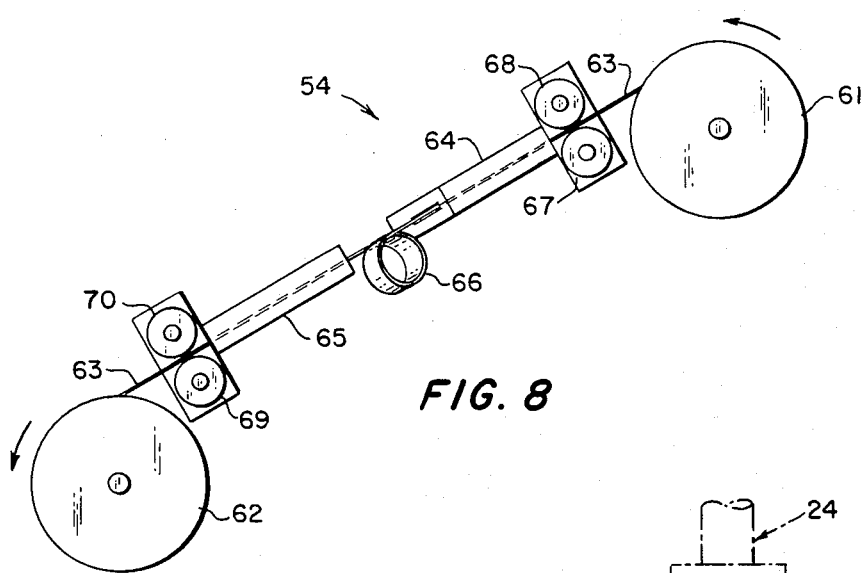
FIG. 8 is a plan view taken along the line of VIII—VIII of FIG. 7 and in the direction of the arrows.
Figure 7:
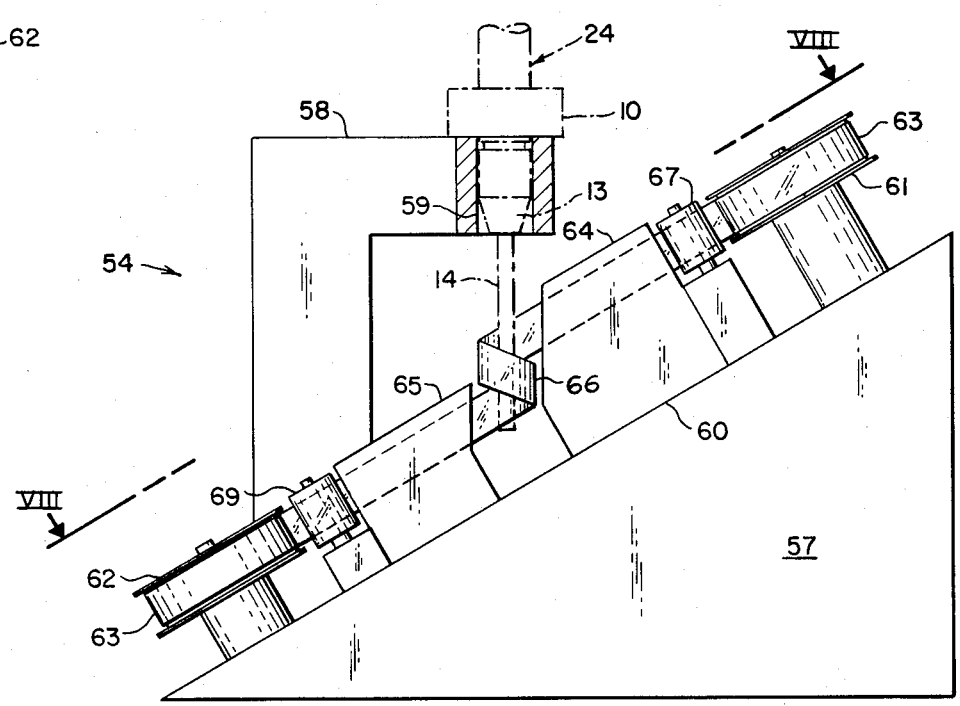
FIG. 7 is a side elevational view of the preferred form of the portion of the apparatus of the present invention by which liquid is removed from the outer surface of a pipette tube, part of the pipette/cuvette being shown in phantom lines.

Referring now to FIG. 1, along with FIG. 5, it will be understood that, because of the lens effect of the meniscus 53 formed by the liquid sample 22 at the lower end of the glass tube 14, it is important for accuracy and reproducibility of absorbance measurements that said meniscus be consistently reproducible. Since, as will hereinafter be apparent, the analyte sample 22 is introduced into tube 14 by aspiration from a quantity thereof in a receptacle, the present invention provides means for removing liquid from the outer surface of the tube 14 after such aspiration to thereby insure reproducibility of the meniscus 53. Absent such removal, liquid on the outer surface of the tube 14 might flow downwardly to the end of the tube and interfere with the formation of a consistent meniscus 53. Removal of such excess liquid is also important to the proper operation of the embodiment of the invention adapted for fluorescent radiation measurement, as will hereinafter appear. FIGS. 7 and 8 illustrate the presently preferred form of apparatus for removal of liquid from the outer surface of the outer end portion of a pipette tube, and FIGS. 9 and 10 illustrate another embodiment of such apparatus.

Referring now to FIG. 7, the apparatus 54 illustrated therein comprises a base member 57 and a support member 58 formed with a bore 59. The support member 58 is adapted to receive and support a pipette/cuvette device 24 as shown in phantom lines in FIG. 7. The base member 57 has an inclined upper surface 60 above which are mounted a supply spool 61 and a take-up spool 62 for a tape 63 extending therebetween. The tape 63 may be made of any suitable absorbent material, for example hydrophilic foam plastic or bibulous paper. The tape 63 passes through guide members 64 and 65 mounted on base member 57 and is formed with a central helical loop portion 66 as shown.

As shown in FIGS. 7 and 8, mounted between the guide member 64 and supply spool 61 is a drive roller 67 and a cooperating pressure roller 68 between which the tape 63 passes. Similarly disposed between the guide member 65 and take-up spool 62 is a drive roller 69 and cooperating pressure roller 70 between which the tape 63 passes. As is well known in the tape transport art, the supply spool 61 may be mounted as an idler, and the take-up spool 62 may be continuously driven from a suitable source through a slip clutch mechanism (not shown) permitting a predetermined maximum tension to be exerted on the tape 63. The drive rollers 67 and 69 are also driven at appropriate times from suitable sources under the control of appropriate control means well known in the art.

With the tape loop 66 of the size shown in FIGS. 7 and 8, insertion axially therethrough of the glass tube 14 of device 24 can be accomplished by coaxial placement of said device in the bore 59 of support member 58. Removal of liquid from the outer surface of the tube 14 is accomplished by pressing the tape 63 into contact therewith. Such pressing contact is effected by reducing the diameter of the loop 66 to that of the outer surface of the tube 14 so that a snug wicking contact therewith results.

This diameter reduction is effected by advancing movement of the drive roller 69, while drive roller 67 is held stationary. If desired, the drive roller 69 may have a slip clutch in its driving connection to prevent excessive tension from being exerted on the tape 63. Once the liquid on the outer surface of the tube 14 has been absorbed by the tape 63 pressed in contact therewith, the size of the loop 66 can then be returned to the diameter shown in FIGS. 7 and 8 by advancing movement of the drive roller 67 while the drive roller 69 is held stationary. The device 24 can then be removed from the support member 58 and moved to the fixture 47 shown in FIG. 5 for absorbance measurement. The tape 63 is then advanced to bring a fresh portion thereof into the loop 66 by simultaneous advancing movement of the pressure rollers 67 and 69 at the same rate of speed. The apparatus 54 is then ready to be used for removal of liquid from the outer surface of the tube 14 of a succeeding device 24.

FIGS. 9 and 10 illustrate semi-diagrammatically another form of apparatus 71 useful for removal of liquid from the outer surface of the tube 14 of a device 24. Apparatus 71 comprises a base member 72 on which are suitably mounted a supply spool 73 and a take-up spool 74 wound around which and extending between which are absorbent tapes 75 and 76 which may be similar to the tape 63 in FIGS. 7 and 8. Extending upwardly from the base 72 are a pair of cylindrical tapespacing members 77 and 78 which normally hold the portions of the tapes 75 and 76 extending between the said members in laterally spaced relation as shown.

Interposed between the member 78 and supply spool 73 are a drive roller 79 and a cooperating pressure roller 80. Similarly interposed between the take-up spool 74 and the member 77 is a drive roller 81 and a cooperating pressure roller 82. The supply spool 73 is preferably an idler, whereas the take-up spool 74 may be continuously driven through a slip clutch mechanism which limits the maximum tension which can be exerted by this spool 74 on the tapes 75 and 76 wound thereon. Also mounted on the base member 72 is an upstanding support member 83 having a vertical bore 84 therein. The member 83 is adapted to support a pipette/cuvette device 24 placed in the bore 84 thereof as shown in phantom lines in FIG. 9. With the device 24 thus supported, the glass tube 14 thereof extends downwardly with its lower end disposed between the adjacent portions of the spaced tapes 75 and 76 as shown.

Means is provided for moving the portions of the tapes 75 and 76 adjacent the tube 14 into snug contact with the outer surface of the tube 14 so that said tape portions absorb liquid on the outer surface of said tube. To this end, the apparatus 71 is provided with aligned pressure members 85 and 86 mounted on opposite sides of the tapes 75 and 76 as shown. The facing edge portions of the members 85 and 86 are formed with complemental semi-cylindrical notches 87 and 88, respectively, which notches have a radius only slightly larger than the radius of the outer surface tube 14. Members 85 and 86 are suitably mounted for reciprocal movement toward and away from each other. Such movement may be effected by any suitable actuating means, solenoid actuating mechanisms 89 and 90 being shown diagrammatically associated with the members 85 and 86, respectively.

FIG. 10 illustrates how the portions of the tapes 75 and 76 adjacent the tube 14 are pressed into contact with the outer surface of the lower end of the tube 14 by movement of the members 85 and 86 toward each other. Upon retraction of the members 85 and 86 to their positions shown in FIG. 9, the tapes 75 and 76 will return generally to the positions thereof shown in that figure, and the device 24 can be removed and transferred to the fixture 47 shown in FIG. 5 for absorbance measurement. The tapes 75 and 76 are then advanced by simultaneous operation of the drive rollers 79 and 81 to bring a fresh portion of each of tapes 75 and 76 between the spacer members 77 and 78. A succeeding device 24 may then be placed in the bore 84 of the support member 83 for removal of liquid from the outer surface of tube 14 thereof.

It will be apparent to those skilled in the art that the apparatus 54 of FIGS. 7 and 8 and the apparatus 71 of FIGS. 9 and 10, when provided with appropriate, well-known control means, are both well adapted to automated procedures.

The use of the apparatus of the present invention in the analysis of a liquid biological analyte sample by a procedure involving optical absorbance measurement will now be described, it being understood that the light guide member 17 is of a sufficient length and flexibility to permit facile movement and manipulation of the pipette/cuvette device 24 during the course of the procedure. With the parts of the device 24 in the position thereof shown in FIG. 2, the outer end of the glass tube 14 is placed into a liquid analyte sample of biological fluid, and by retractile movement of the plunger 2 and thereby of piston 16, a precisely measured quantity of the analyte is aspirated into the tube 14. The device 24, with the measured sample in the tube 14, is then transferred to the mechanism shown in FIGS. 7 and 8 or that shown in FIGS. 9 and 10, and by operation of such mechanisms in the manner described, the liquid analyte adhering to the outer surface of the tube 14 is removed by the absorbent tape as a result of a wicking action. This provides a precise meniscus 53 in the sample as shown in FIG. 1, and the device 24 is then transferred to the fixture 47 shown in FIG. 5.

The lamp 18 of the light source means 31 shown in FIG. 4 is then illuminated, and, as shown by the broken lines in FIG. 1, light therefrom travels through the filter 19, the condenser lens assembly 20, and the fiber optic light guide 17 to the measured liquid analyte sample in tube 14 identified by the number 22. It will be observed that the tube 14 and the liquid sample 22 function as a light guide similar in operation to the light guide member 17, and that the light emitted from the tube 14 is directed toward the photodetector 21. The amount of light reaching the photodetector 21 is indicated or recorded by suitable readout means (not shown). The device 24 is then removed from the fixture 47 and the outer end of the tube 14 thereof is then placed in a suitable mixing receptacle (not shown). The measured analyte is then dispensed into the mixing receptacle by depression of the plunger 2 which causes return of the parts of the device 24 to the position shown in FIG. 2.

The outer end of the tube 14 of device 24 is then placed in a liquid reagent to be used in the analytical method, and a precisely measured volume thereof is aspirated into the tube 14 by retractile movement of the plunger 2 and corresponding retractile movement of piston 16. The outer end of the tube 14 is then placed in the mixing receptacle and the measured reagent portion is dispensed thereinto by advancing movement of the plunger 2 and piston 16 sufficient to return the parts of the device 24 to the postion shown in FIG. 2.

The measured analyte and reagent portions in the mixing receptacle are then mixed by successive aspiration thereof into the tube 14 and dispensing thereof into the mixing receptacle in response to successive retractile and advancing movement of the plunger 2 while the outer end of the tube 14 is in the combined liquids. The mixed sample and reagent are then incubated, if necessary, and a precisely measured quantity of the mixed sample and reagent is then aspirated into the tube 14 by retractile movement of the plunger 2 and piston 16 while the outer end of said tube is in the mixed liquids.

The device 24 is then transferred to the apparatus of FIGS. 7 and 8 or 9 and 10 for removal, in the manner aforedescribed, of any liquid on the outer surface of the end portion of the tube 14. Device 24 is then placed on the fixture 47 of FIG. 5, and the optical absorbance of the mixed analyte and reagent in the tube 14 is measured, i.e., the light from source 18 not absorbed by the liquid in the tube 14 is directed onto the photodiode 21 for measurement and recordal as aforedescribed. The difference between the amount of light which is transmitted through the precisely measured volume of unmixed analyte sample to the photodetector 21 and the amount of light which is transmitted through the same precise volume of mixed analyte and reagent to said photodetector provides meaningful optical absorbance data indicating the presence and/or amount of a particular biochemical component in the analyte sample. The optical absorbance is measured at the particular wavelength in the UV to IR range of the electromagnetic spectrum permitted to pass through the selected filter 19.

Figure 6:
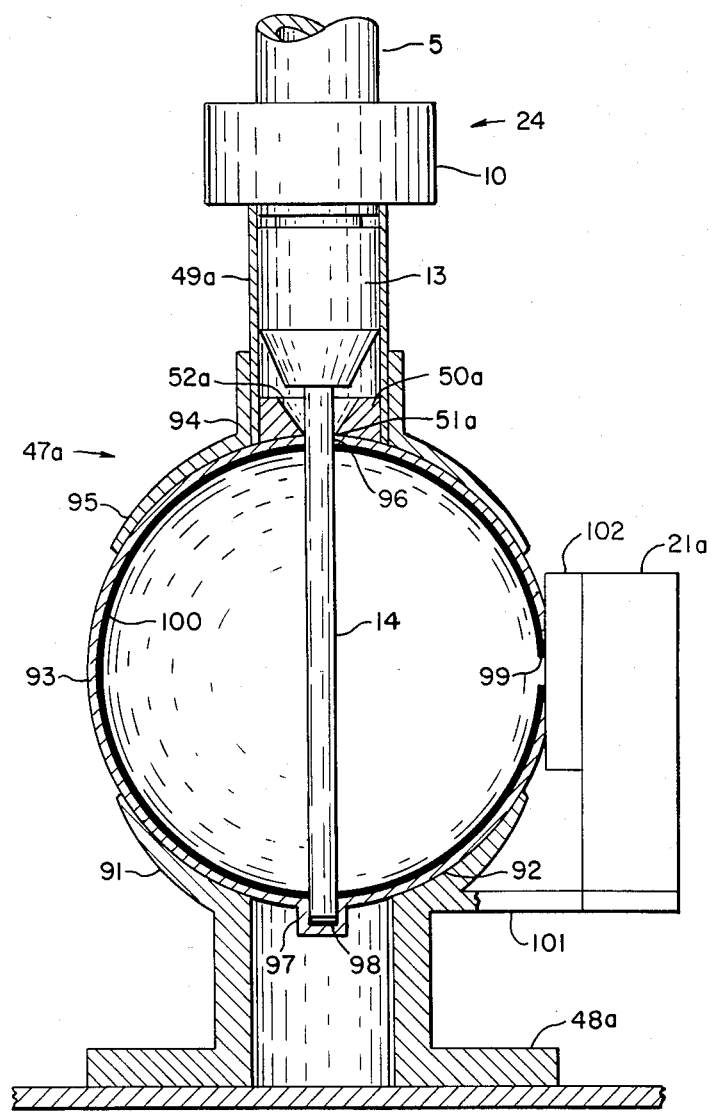
FIG. 6 is a vertical sectional view similar to FIG. 5 taken through the radiation measurement fixture portion of an embodiment of the present invention adapted for fluorescent radiation measurement, part of the pipette/cuvette being shown in operative position within said fixture.

The pipette/cuvette device 24 is also well adapted for use in measurement of fluorescent radiation resulting from flash-type monochromatic irradiation of a fluorescent analyte sample, and FIG. 6 illustrates a form of the apparatus of the present invention which is particularly adapted for such radiation measurement. In FIG. 6 the parts indicated by reference numerals with the suffix "a" correspond in general to parts of the fixture 47 (FIG. 5) indicated by the same reference numerals without a suffix.

More particularly, FIG. 6 illustrates a fixture 47a comprising a tubular base member 48a formed at its upper end with an outwardly and upwardly projecting annular flange portion 91 having a concave upper surface 92. Supported on the surface 92 is an integrating sphere 93, the outer surface of which has a radius of curvature complemental to that of the surface 92. Mounted on the sphere 93 diametrically opposite the flange 91 is a tubular fitting 94 having a downwardly facing concave annular flange 95 which is generally similar to flange 91. Telescopically fitted into the fitting 94 is a barrel member 49a. Fixed within the lower end of barrel 49a is a cylindrical guide member 50a having a frusto-conical bore 52a extending axially therethrough and terminating at its lower end in a circular opening 51a which is of a size to slidably receive therethrough the glass tube 14 of device 24.

The sphere 93 is formed with a bore 96 therethrough which is of the same diameter and is coaxial with the circular opening 51a. Diametrically opposite the bore 96 the sphere 93 is formed with a cylindrical cup-shaped radially outwardly offset portion 97 having a flat inner surface 98. The offset portion 97 has an inner diameter of a size to slidably receive the outer end of tube 14 of device 24 telescopically therein.

The sphere 93 is formed with a radiation exit opening 99 offset substantially ninety degrees from the bore 96 and offset portion 97. High reflectance is provided to the inner surface of the sphere 93 as well as to the flat inner surface 98 of offset 97, for example, by a layer 100 of highly reflective material such as magnesium oxide or barium sulfate, or by other suitable means.

The base member 48a is provided with a lateral projection 101 for supporting a photodetector 21a which preferably takes the form of a side viewing photomultiplier or photodiode. The photodetector is positioned to receive radiation emitted from the sphere 93 through exit opening 99, and interposed between said photodetector and the sphere 93 is a narrow bandpass interference filter 102.

The light source appropriate for the production of fluorescent radiation is different from the incandescent source 18 illustrated in FIGS. 1 and 4. More Particularly, when the apparatus of FIG. 6 is used, the source 18 preferably takes the form of a short arc xenon flash lamp capable of producing a short, e.g., $10^{-8}$ seconds, very intense flash of light. A lamp satisfactory for this purposes is the FX332 lamp made by the Electro-Optics Division of E.G. & G., Inc., 35 Congress Street, Salem, Mass.

The filter 19 used for fluorescent radiation measurement is one which has high light transmittance at the optimum excitation wavelength of the particular fluorescent analyte sample (fluorophore) whose fluorescent radiation is to be measured, and which does not transmit light having a wavelength longer than said excitation wavelength. On the other hand, the filter 102 in FIG. 6 is one which has high light transmittance at the fluorescent emission wavelength of the particular fluorophore whose fluorescent radiation is to be measured, and which does not transmit light of a shorter wavelength. Since the excitation wavelength is substantially shorter than the fluorescent emission wavelength, radiation of the excitation wavelength is prevented from passage through the filter 102, whereas radiation of the fluorescent emission wavelength is readily tramsmitted through filter 102.

The optimum excitation radiation wavelength and the wavelength of the resultant fluorescent emission varies for different fluorophores. Table 1 lists such wavelengths for several of the more common fluorophores and can serve as the basis for selection of the commercially available filters to be used as filters 19 and 102.

TABLE 1

| Fluorophore | Excitation Wavelength (nm) | Fluorescent Emission Wavelength (nm) |
|---|---|---|
| Tryptophan | 275 | 348 |
| 1-Naphthol | 335 | 455 |
| NADH | 340 | 435 |
| Quinine | 350 | 450 |
| Umbelliferone | 365 | 450 |
| Umbelliferone-3-Carboxamide | 405 | 450 |
| Acridine | 450 | 530 |
| Riboflavin | 455 | 525 |
| Florescein | 480 | 520 |
| Resorufin | 540 | 580 |

TABLE 1-continued

| Fluorophore | Excitation Wavelength (nm) | Fluorescent Emission Wavelength (nm) |
|---|---|---|
| Rhodamine B | 550 | 605 |

In the measurement of fluorescent radiation the fiber optic light guide 17 used is one which is capable of transmitting light of frequencies extending into the UV range. Suitable materials are commercially available for this purpose, such as quartz, glass and organoplastic.

Since the intensity of fluorescent light emitted from a fluorescent analyte is orders of magnitude lower than that of the incident excitation radiation, the need to more effectively collect fluorescent radiation has led to the development of the integrating sphere-type fluorimeter of the type disclosed by W. R. Ware and W. Rothman in Chem, Phys. Letters 39 (1976) 49. In that instrument a conventional cuvette is located centrally of the integrating sphere, and the fluorescent radiation emitted by the analyte in the cuvette is reflected by the sphere walls until it is absorbed by a photodetector or lost through the incident beam entrance opening.

As shown in FIG. 6, when the pipette/cuvette device 24 is in operative position on the fixture 47a, the tube 14 containing the analyte sample or mixed analyte and reagent extends diametrically across the interior of the integrating sphere 93. In carrying out an analysis involving fluorescent radiation measurement by the use of the apparatus of the present invention, the procedure followed for measurement of analyte and reagent and mixing thereof, as well as for removal of liquid from the outer surface of the end portion of tube 14, are generally the same as has been described in connection with procedures used for absorbance measurements.

The pipette/cuvette device 24 containing the measured analyte or mixed analyte and sample is placed in the operative position shown in FIG. 6 by inserting the tube 14 generally coaxially into the upper end of barrel 49a and downwardly through the guide member 50a, opening 51a and bore 96. As the tip of tube 14 approaches the offset portion 97 on continued downward movement, the cylindrical compression nut 13 of device 24 fits telescopically within barrel 49a to thereby guide the tip of tube 14 telescopically into the cylindrical offset portion 97 until device 24 comes to rest when collar 10 contacts the upper end of barrel 49a.

The xenon flash lamp 18 now in light source means 31 is then energized to produce a very intense flash of light of short duration, i.e., $10^{-8}$ seconds. This flash of light travels through filter 19 which permits passage therethrough of only that wavelength of light which is the optimum for excitation of the particular fluorophore in the liquid in tube 14. The monochromatic light leaving filter 19 travels through the condenser lens assembly 20 and fiber optic light guide 17 to and through the liquid in tube 14. The light strikes the highly reflective inner surface 98 of offset 97 and is reflected back through the liquid, thereby illuminating said liquid twice with each flash.

Absorption of this radiant energy by the molecules of fluorophore in the liquid in tube 14 raises the vibrational level of such molecules from the ground state to one of the excited electronic levels. This absorption occurs within $10^{-15}$ seconds, and fluorescence results from the spontaneous radiative transition which occurs when the molecules of the fluorophore returns to the ground electronic state upon cessation of the flash of incident excitation radiation. The resulting fluorescent light is given off equally in all directions and at the wavelength typical of the particular fluorophore, for example as set forth in Table 1.

The fluorescent radiation emitted from the liquid in tube 14 is reflected by the highly reflective inner surface 100 until it passes out the opening 99 and into the filter 102. Filter 102 blocks passage therethrough of incident light at the excitation wavelength which would interfere with accurate measurement of the fluorescent radiation if such excitation wavelength radiation were permitted to reach the photodetector 21a along with the fluorescent radiation. The fluorescent radiation thus passes through filter 102, and the amount thereof reaching photodetector 21a is indicated or recorded by suitable readout means (not shown).

The apparatus and method of the present invention are substantial improvements over prior art optical absorbance and fluorescent radiation measurement apparatus and methods. Of particular importance is the fact that the device 24 serves, not only as a precision liquid pipetting device for the measurement and mixing of analyte and reagent, but it also functions as a cuvette in which the combined analyte and reagent are contained during optical absorbance or fluorescent radiation measurements. As best shown in FIG. 1, substantially all of the liquid in the tube 14 is subjected to the irradiating light. This contrasts with conventional cuvettes in which the irradiating light beam passes through only a limited portion of the contained liquid.

It is also apparent from FIG. 1 that the device 24 provides the longest possible light path length for a given volume of liquid, and that the irradiation of the liquid is maximized by the multiple internal reflections through the liquid, which reflections also minimize incident light loss.

Another feature of the apparatus of the present invention is that the volume of the liquid in the tube 14 and the optical path length therethrough can be precisely and infinitely varied to accommodate the optical density of the particular liquid by the simple expedient of selection of the retracted position of the piston 16. This obviates the need for either diluting the liquid or substituting a cuvette of different optical path length.

The apparatus shown in FIGS. 7 to 10, by removing liquid from the outer surface of the outer end portion of the tube 14, not only provides for precise meniscus formation at the outer end of said tube, but it also minimizes liquid cross-contamination between successive analyzing method sequences, as well as preventing contamination of portions of the fluorescent radiation measurement apparatus, particularly in the area of the offset 97 of sphere 93.

The apparatus of the present invention has demonstrated remarkable reproducibility in light absorbance measurement. More particularly, the apparatus shown in FIGS. 1 to 5 and the described absorbance measurement method were tested for reproducibility of light measurement using a series of two-fold dilutions of dye in water. The apparatus demonstrated a reproducibility in light measurement down to the noise level of the electronic light measurement circuitry used, which was 1.2 percent. It is logical to assume that had a more sensitive electronic circuit been used which had a lower noise level, even greater reproducibility would have been demonstrated.

Various changes, adaptations and modifications of the illustrated embodiments of the invention will be apparent to those skilled in the art and may be made without departing from the spirit of the invention. All of such changes, adaptations and modifications are contemplated as may come within the scope of the appended claims.

What is claimed as the invention is:

1. The method of analysis using a pipette tube or the like having an open end and a piston movable axially within said pipette tube between a first position at said open end and a retracted position spaced from said open end for aspiration of liquid into or dispensing liquid from said pipette tube through said open end, said method comprising the steps of aspirating a predetermined volume of liquid into said pipette tube, directing radiation from said piston axially through substantially all of the liquid aspirated, and measuring the radiation emitted from the irradiated liquid in the pipette tube.

2. The method of claim 1 wherein the radiation measured is that which is emitted from said liquid through the open end of the pipette tube.

3. The method of claim 1 wherein the radiation measured is that which is emitted from said liquid through the wall of the pipette tube.

4. The method of claim 1 wherein, prior to irradiating the liquid in the pipette tube, said tube is inserted into an integrating sphere having an access opening therefor and also having a radiation outlet opening, and the radiation measured is that which passes through said radiation outlet opening.

5. The method of claim 1 wherein, following aspiration of the liquid into the pipette tube, the meniscus formed by the aspirated liquid at the open end of the tube is protected by contacting the outer surface portion of the tube adjacent said open end with a bibulous material to remove liquid therefrom.

6. The method of claim 1 wherein the liquid comprises the product resulting from the combination of an analyte and at least one reagent.

7. The method of claim 1 wherein the piston comprises one end portion of a radiation guide member which extends from said pipette tube, and radiation is directed into the radiation guide member at a point outside the tube.

8. The method of claim 1 wherein the piston comprises one end portion of a fiber optic radiation guide member which extends from said pipette tube, and radiation is directed into the fiber optic guide member at a point outside the tube.

9. The method of claim 1 wherein, following aspiration of the liquid into the pipette tube, the meniscus formed by the aspirated liquid at the open end of the pipette tube is protected by removal of liquid on the outer surface portion of the tube adjacent said open end, said liquid removal being effected by the method comprising the steps of supporting portions of dry bibulous material in standby positions at a work station wherein said portions are sufficiently spaced apart to permit ready interposition of the open end portion of the pipette tube therebetween, placing the open end portion of the tube between said spaced apart bibulous material portions, moving said bibulous material portions from said standby positions into conforming contact with the outer surface portions of said tube, withdrawing said bibulous material portions from contact with said tube, and thereafter removing said bibulous material portions from said standby positions and substituting therefor in said standby positions replacement portions of dry bibulous material.

10. The method of claim 1 wherein the radiation measured is that which is emitted through the wall of the pipette tube, said method additionally comprising reflecting back into said tube through said open end radiation emitted from said tube through said open end.

11. The method of analysis using a pipette tube or the like having an open end and a piston movable axially within said pipette tube between a first portion at said open end and a retracted position spaced from said open end for aspiration of liquid into or dispensing of liquid from said tube through said tube end, said method comprising placing a predetermined volume of liquid analyte and a predetermined volume of liquid reagent in a mixing receptacle, mixing the analyte and reagent placed in said receptacle, aspirating a predetermined volume of the combined liquids from the mixing receptacle into said tube, directing radiation from said piston axially through substantially all of the liquid aspirated, and measuring the radiation emitted from the irradiated liquid in the tube.

12. The method of claim 11 wherein, prior to irradiating the liquid in the pipette tube, the open end of said tube is placed in alignment with and in juxtaposition to radiation sensing means, and the radiation measured is that which is emitted from the liquid through the open end of the pipette tube and is sensed by said sensing means.

13. The method of claim 11 wherein the radiation measured is that which is emitted from the liquid through the wall of the pipette tube.

14. The method of claim 11 wherein, prior to irradiating the liquid in the pipette tube, said tube is inserted into an integrating sphere having an access opening therefor and also having a radiation outlet opening at which radiation sensing means is disposed, and the radiation measured is that which passes through said radiation outlet opening and is sensed by said sensing means.

15. The method of claim 11 which also includes separately aspirating into said pipette tube an amount of said liquid analyte equal to said predetermined volume thereof, directing radiation from said piston axially through substantially all of the liquid analyte aspirated into the tube, and measuring the radiation emitted from the irratiated liquid analyte in the tube.

16. The method of claim 11 wherein the liquid analyte and reagent are mixed by aspirating liquid from the receptacle into the pipette tube and dispensing said liquid back into the receptacle.

17. The method of claim 11 wherein, after aspiration of the predetermined volume of the combined liquids into the pipette tube, the meniscus formed by the aspirated liquid at the open end of the tube is protected by contacting the outer surface portion of the tube adjacent said open end with bibulous material to remove liquid therefrom.

18. The method of claim 11 wherein, prior to irradiating the combined liquids, the meniscus formed by the aspirated liquid at the open end of the pipette tube is protected by contacting the outer surface portion of the tube adjacent said open end with bibulous material to remove liquid therefrom, said method also including separately aspirating into said pipette tube an amount of liquid analyte equal to said predetermined volume thereof, protecting the meniscus formed by the aspirated analyte at the open end of the tube by contacting the outer surface portion of the tube adjacent said open end with bibulous material to remove liquid therefrom, directing radiation from said piston axially through substantially all of the liquid analyte aspirated into the tube, and measuring the radiation emitted from the irradiated liquid analyte in the tube.

19. The method of claim 11 wherein, after aspiration of the predetermined volume of the combined liquids into the tube, the meniscus formed by the aspirated liquid at the open end of the pipette tube is protected by removal of liquid on the outer surface portion of the tube adjacent said open end by the method comprising the steps of supporting portions of dry bibulous material in standby postions at a work station wherein said portions are sufficiently spaced apart to permit ready interposition of the open end portion of the pipette tube therebetween, placing the open end portion of the tube between said spaced apart bibulous material portions, moving said bibulous material portions from said standby positions into conforming contact with outer surface portions of said tube, withdrawing said bibulous material portions from contact with said pipette tube, and thereafter removing said bibulous material portions from said standby positions and substituting therefor in said standby positions replacement portions of dry bibulous material.

20. The method of claim 11 wherein the radiation measured is that which is emitted through the wall of the pipette tube, said method additionally comprising reflecting back into said tube through said open end radiation emitted from said tube through said open end.

21. In combination, a cylindrical pipette tube or the like having an open end, a piston movable axially within said tube between a first position at said open end and a retracted position space from said open end for aspiration of liquid into said tube and dispensing of liquid from said tube through said open end, and radiation source means incorporated with said piston for directing radiation from said piston generally axially within said pipette tube and through substantially all of the liquid contained therein.

22. The combination of claim 21 wherein said radiation source means comprises a radiation guide having an end portion incorporated with and terminating at the outer end of said piston.

23. The combination of claim 21 wherein said radiation source means comprises a radiation guide having an end portion incorporated with and terminating at the outer end of said piston and having a portion remote therefrom adapted to receive radiation.

24. The combination of claim 21 wherein said radiation source means comprises a radiation source, and a radiation guide having one end portion incorporated with and terminating at the outer end of said piston, the other end of said guide being positioned to receive radiation from said source.

25. The combination of claim 21 wherein the radiation source means comprises a fiber optic member having an end portion extending axially through, incorporated with and terminating at the outer end of said piston, said fiber optic member extending from said pipette tube and having an opposite end portion adapted to receive radiation.

26. The combination of claim 21 wherein the pipette tube is formed of glass, quartz, or organoplastic.

27. The combination of claim 21 which also includes radiation detection means adapted to sense radiation emitted from the open end of the pipette tube.

28. The combination of claim 21 which also includes radiation detection means adapted to sense radiation emitted through the wall of the pipette tube.

29. The combination of claim 21 which also includes means for protecting the meniscus formed at the open end of the pipette tube by liquid aspirated into the tube, comprising means for contacting the outer surface of the end portion of the tube with bibulous material to remove liquid therefrom.

30. The combination of claim 21 which includes means for protecting the meniscus formed at the open end of the pipette tube by liquid aspirated into the tube, comprising means for contacting the outer surface of the end portion of the tube with bibulous material to remove liquid therefrom, and radiation detection means adapted to sense radiation emitted from the tube.

31. The combination of claim 21 which also includes means for protecting the meniscus formed at the open end of the pipette tube by liquid aspirated into said tube, comprising means for removing liquid from the outer surface of the open end portion of the pipette tube, said means comprising means for supporting portions of dry bibulous material in standby positions at a work station wherein said portions are sufficiently spaced apart to permit ready interposition of the open end portion of the pipette tube therebetween, and actuating means for moving said bibulous material portions from said standby positions into contact with outer surface portions of the pipette tube when the latter is disposed between said bibulous material portions in said standby position, means for retracting said bibulous material from contact with said pipette tube to said standby positions, and means for substituting for the retracted portions of bibulous material replacement portions of dry bibulous material in said standby positions.

32. The combination of claim 21 which also comprises radiation detection means adapted to sense radiation emitted through the wall of the pipette tube, and reflective means for reflecting back into said tube through the open end thereof radiation emitted from said tube through said open end.

33. The combination with a pipette/cuvette device having a generally cylindrical end portion, having a cylindrical pipette tube projecting coaxially from said end portion and terminating in an open end, and having a piston movable axially within said pipette tube between a first position at said open end and a retracted position spaced from said open end for aspiration of liquid into said pipette tube and dispensing of liquid from said pipette tube through said open end, said piston incorporating light source means, of a fixture having a generally cylindrical tubular portion provided with an open end adapted to removably telescopically receive in operative position therein the cylindrical end portion of said pipette/cuvette device after insertion thereinto of said cylindrical pipette tube, said fixture including radiation detection means positioned to receive radiation emitted from said pipette tube when the pipette/cuvette device is in said operative position.

34. The combination of claim 33 wherein said radiation detection means is positioned in alignment with the open end of said pipette tube when said pipette/cuvette device is in said operative position.

35. The combination of claim 33 wherein said fixture comprises an integrating sphere within which said pipette tube is disposed when said pipette/cuvette device is in said operative position, said integrating sphere having a radiation outlet opening, and said radiation detection means is positioned at said radiation outlet opening.

36. The combination of claim 33 wherein said fixture comprises an integrating sphere within which said pipette tube is disposed when said pipette/cuvette device is in said operative position for emission of radiation thereinto through the wall of said pipette tube, said integrating sphere having a radiation outlet opening at which said detection means is positioned to receive radiation, said sphere also having reflective means positioned to reflect axially into the open end of the pipette tube radiation emitted axially from said open end when the pipette/cuvette device is in said operative position.

* * * * *